United States Patent [19]

Ganguly et al.

[11] Patent Number: 4,690,922

[45] Date of Patent: *Sep. 1, 1987

[54] 2-(HETEROCYCLOALKYLTHIO)PENEMS

[75] Inventors: Ashit K. Ganguly, Upper Montclair; Viyyoor M. Girijavallabhan, Parsippany; Patrick A. Pinto, Mine Hill; Richard W. Versace, Ringwood, all of N.J.

[73] Assignee: Schering Corporation, Kenilworth, N.J.

[ * ] Notice: The portion of the term of this patent subsequent to Sep. 30, 2003 has been disclaimed.

[21] Appl. No.: 626,820

[22] Filed: Jul. 2, 1984

Related U.S. Application Data

[63] Continuation-in-part of Ser. No. 564,586, Dec. 22, 1983, abandoned, which is a continuation-in-part of Ser. No. 475,281, Mar. 14, 1983, abandoned.

[30] Foreign Application Priority Data

Feb. 29, 1984 [DK] Denmark .............................. 1417/84
Mar. 7, 1984 [EP] European Pat. Off. ......... 84102429.2

[51] Int. Cl.$^4$ ................. C07D 499/00; A61K 31/425

[52] U.S. Cl. .................................... 514/210; 540/310; 540/350

[58] Field of Search ................. 260/245.2 R, 245.2 T; 424/270, 271; 540/350, 310; 514/210

[56] References Cited

U.S. PATENT DOCUMENTS

| | | | |
|---|---|---|---|
| 4,301,074 | 11/1981 | Christensen et al. | 424/270 |
| 4,423,055 | 12/1983 | McCombie | 260/245.2 R |
| 4,431,658 | 2/1984 | Afonso et al. | 260/245.2 R |
| 4,435,412 | 3/1984 | Girijavallabhan | 424/270 |
| 4,559,333 | 12/1985 | Girijavallabhan et al. | 540/310 |
| 4,587,241 | 5/1986 | Girijavallabhan et al. | 540/310 |
| 4,614,738 | 9/1986 | Girijavallabhan et al. | 514/194 |

OTHER PUBLICATIONS

Derwent Abstract 881012 10/1979.

*Primary Examiner*—Nicholas S. Rizzo
*Attorney, Agent, or Firm*—Anita W. Magatti; Stephen I. Miller; Gerald S. Rosen

[57] ABSTRACT

This invention relates to 2-(heterocycloalkylthio)-penems wherein the nitrogen of the heterocyclic ring is connected to the alkyl group, and to their use as antibacterial agents.

34 Claims, No Drawings

2-(HETEROCYCLOALKYLTHIO)PENEMS

This application is a continuation-in-part of copending application Ser. No. 564,586, filed Dec. 22, 1983, now abandoned which is a continuation-in-part of Ser. No. 475,281, filed Mar. 14, 1983 now abandoned.

BACKGROUND OF THE INVENTION

This invention relates to 2-(heterocycloalkylthio)-penems and their pharmaceutically acceptable salts and esters, which compounds possess potent anti-bacterial activity.

There is a continuing need for new antibacterial agents because continued extensive use of effective antibacterials gives rise to resistant strains of pathogens.

SUMMARY OF THE INVENTION

This invention relates to novel 2-(heterocycloalkylthio)penems wherein a nitrogen of the heterocyclic ring is connected to the alkyl group, and to their use as antibacterial agents. More particularly, this invention relates to 6-(1-hydroxyethyl)-2-(heterocycloalkylthio)-penem-3-carboxylic acids represented by the formula

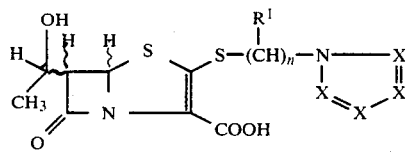

wherein each X is

or =N—, with the proviso that at least one X is

R is hydrogen, lower alkyl, amino lower alkyl, mono- and di-lower alkyl amino lower alkyl, carboxy lower alkyl, sulfoalkyl, hydroxyalkyl, cyano, hydroxy, amino, mono- and di-lower alkyl amino, alkyl sulfonate, sulfamyl, halogeno, hydroxyliminoloweralkyl, lower alkoxyiminoloweralkyl, carboxy, carbamoyl, mono- or di-lower alkyl carbamoyl, nitro, carbamoyloxy, ureido lower alkyl, or carbamoylhydrazolower alkyl;

$R^1$ is hydrogen, lower alkyl, carboxy, carbamoyl, cyano, hydroxy, amino, lower alkylthio, fluoro, lower alkoxy, or lower alkanoyloxy, provided that when $R^1$ is attached to a carbon atom adjacent to S or N, $R^1$ is not hydroxy, amino, or fluoro; or $R^1$ is lower alkyl substituted by hydroxy, cyano, halogen, lower alkoxy, carbamoyloxy, —$SR^2$, imidazolyl, substituted imidazolyl wherein the substituents are as defined by R, amino, amino substituted by lower alkyl, lower alkyl carbonyl, carbamoyl, mono-alkyl substituted carbamoyl or ureido, carboxy, carbamoyl, mono-alkyl substituted carbamoyl, lower alkylcarbonyl, lower alkoxycarbonyl, hydroxy lower alkyl carbonyl, sulfo, sulfamyl, lower alkyl thio, lower alkylsulfonyl, lower alkoxysulfonyl, or hydroxy lower alkylsulfonyl;

$R^2$ is substituted or unsubstituted single ring or double fused ring heterocyclyl;

n is 1 to 4; and the pharmaceutically acceptable salts and esters thereof, in racemic or optically active form.

Preferred compounds of formula A are those wherein the nitrogen-containing heterocyclic group is selected from the group consisting of unsubstituted or substituted pyrrolyl, imidazolyl, pyrazolyl, 1,2,4-triazolyl, 4,1,2-triazolyl, 1,2,3-triazolyl, 2,1,3-triazolyl, 1,2,3,4-tetrazolyl and 2,1,3,4-tetrazolyl, wherein the substituents are 1 to 4 R groups. More preferred are compounds of formula A wherein the nitrogen containing heterocyclic is imidazolyl or triazolyl.

Also contemplated are five membered nitrogen-containing aromatic groups (attached to the rest of the penem molecule through a ring nitrogen) to which are fused a second aromatic ring, preferably a six-membered aromatic ring containing 0-3 nitrogen atoms in the ring. Examples of such fused ring groups are purinyl (i.e. 1,3,4,6-benzotetrazolyl), indolyl, isoindolyl, isoindazolyl, benzimidazolyl, indazolyl, 1,2,3-benzotriazolyl, 2,1,3-benzotriazolyl, 4,5,6 or 7-azaindolyl, 4,5,6 or 7-azabenzimidazolyl, 4,5,6 or 7-azabenzopyrazolyl, 1-pyrazolo-[3,4-d]-pyrimidinyl, 2-pyrazolo-[4,3-c]-pyridinyl, 3-v-triazolo-[4,5-b]-pyridinyl, 1-pyrazolo-[3,4-b]-pyrazinyl, and 2-v-triazolo-[4,5-b]-pyrazinyl.

Preferred $R^1$ substituents are hydrogen and substituted lower alkyl. Preferred substitutents on the lower alkyl group are carbamoyl, amino, lower alkyl carbonylamino, fluoro and cyano.

Preferred R substituents are amino, hydroxy and substituted and unsubstituted lower alkyl. A preferred substitutent on the lower alkyl group is hydroxy.

Also preferred are compounds of formula A wherein n is 2 to 4; more preferred are those compounds wherein n is 2.

The term "lower alkyl" as used herein means alkyl groups of 1 to 6 carbon atoms and includes methyl, ethyl, propyl, butyl, pentyl and hexyl and the corresponding branched chain isomers thereof. Similarly, "lower alkoxy" means straight or branched alkoxy groups having 1 to 6 carbon atoms, e.g., methoxy, ethoxy, propoxy and butoxy, and "lower alkanoyloxy" means straight or branched chain alkanoyloxy groups of 1 to 6 carbon atoms, e.g. acetoxy, propionoxy, and butyryloxy.

As used herein, the term "$SR^2$" refers to single or double fused ring heterocyclyl radicals bonded to a sulfur atom by a ring carbon, wherein said heterocyclyl radicals are selected from the group consisting of benzothiazolyl, oxazinyl, pyridyl, purinyl, imidazolyl, pyrolyl, thiazolyl, thiadiazolyl, benzimidazolyl, triazinyl, thiazinyl, furyl, thienyl, triazolyl, tetrazolyl and pyrimidyl. The heterocycyl radicals include their isomeric forms e.g. 2-pyridyl, 4-pyridyl; 2-furyl, 3-furyl; and 2-pyrimidyl, 4-pyrimidyl. Substituted heterocyclylthio groups are those wherein said heterocycyl rings have one or more substitutent which can be the same or different and (a) are on a ring carbon or heteroatom, and are independently selected from the group consisting of lower alkyl, —$NR^3R^4$, and loweralkylene-$NR^3R^4$, wherein $R^3$ and $R^4$ are independently selected from the group consisting of hydrogen and lower alkyl, or (b) are on a ring carbon atom only and are selected from the group consisting of =O, hydroxy, lower alkoxy, —$COOR^5$ or halogen, wherein $R^5$ is hydrogen, a pharmaceutically acceptable readily metabolizable ester forming substitutent or a pharmaceutically acceptable cation.

Compounds of the present invention possess 3 or more asymmetric carbon atoms, indicated in the partial formula B below at the 5, 6, 8 and 2' to 5'-position carbon atoms.

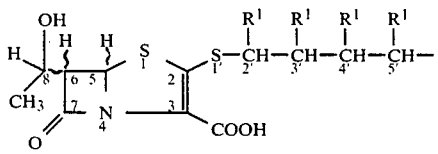

At the 5, 6, and 8 positions, compounds of the invention may possess 5R,6S,8R or 5R,6R,8S stereochemistry at those chiral atoms. The preferred absolute stereochemistry for the compounds of the present invention at those positions is 5R,6S,8R.

Compounds of formula A wherein $R^1$ is other than hydrogen will have additional asymmetric carbon atom(s) as shown in formula B at the 2' to 5' positions. All the possible resulting steroisomers are included herein.

DETAILED DESCRIPTION

When tested in standardized microbiological assays, the compounds of this invention are active against such gram-positive organisms as *Staphylococcus epidermis* and *Bacillus subtilis*, and such gram-negative organisms as *E. coli* and *Salmonella*, at test levels of 0.01 to 1.0 micrograms/ml. Additionally, they show activity against organisms which produce beta-lactamases, e.g., penicillinase and cephalosporinase, indicating a stability toward these enzymes. For instance, 5R,6S,8R-2-[2-(imidazol-1-yl)-ethylthio]-6-(1-hydroxyethyl)penem3-carboxylic acid is active against Enterobacter 72012502 at a test level of 0.250 microgram/ml. When tested against *E. coli* 74081501 TEM-1 (a beta-lactamase producing organism) the compound exhibits activity at 0.031 microgram/ml. When tested against over sixty organisms, the mean test level against gram-negative organisms was 0.135 microgram/ml and against gram-positive organisms was 0.061 microgram/ml.

The compounds of this invention and their metabolites have little or no unpleasant odor.

As antibacterial agents, the compounds of this invention are conventionally formulated for oral, parenteral, topical and transdermal use. Thus, this invention includes within its scope pharmaceutical compositions comprising the compounds of this invention in admixture with a pharmaceutically acceptable carrier therefor. In addition, the present invention also provides a method of treating bacterial infections in animals, particularly warm-blooded animals having a susceptible bacterial infection which comprises administering to said animal an antibacterial effective amount of a compound of this invention, or a pharmaceutical composition thereof. In the foregoing compositions, the compounds of this invention can be used as the sole active antibacterial agent or in combination with other antibacterial agents and/or enzyme inhibitors.

For oral administration, the compounds of this invention are typically formulated in the form of tablets, capsules, elixirs, or the like. For parenteral administration, they may be formulated into solutions or suspensions. Typical topical formulations are those such as lotions, creams, ointments, sprays, and mechanical delivery devices, e.g., transdermal. Parenteral administration is preferred. Typical pharmaceutically acceptable carriers for use in the formulations described above are exemplified by: sugars such as lactose, sucrose, mannitol and sorbitol; starches such as corn starch, tapioca starch and potato starch; cellulose and derivatives such as sodium carboxymethyl cellulose, ethyl cellulose and methyl cellulose; calcium phosphates such as dicalcium phosphate and tricalcium phosphate; sodium sulfate; calcium sulfate; polyvinyl pyrrolidone; polyvinyl alcohol; stearic acid; alkaline earth metal stearates such as magnesium stearate; vegetable oils such as peanut oil, cottonseed oil, sesame oil, olive oil and corn oil; non-ionic, cationic and anionic surfactants; ethylene gylcol polymers; betacyclodextrin; fatty alcohols; hydrolyzed cereal solids; water; polyalkylene gylcols; gums; and petrolatum; as well as other non-toxic compatible fillers, binders, disintegrants and lubricants commonly used in pharmaceutical formulations. The compositions may also contain preservatives, aerosol propellants and coloring, thickening, suspending, dispensing, emulsifying, wetting, stabilizing and buffering agents.

The dosage of the compounds of this invention which is administered is dependent on the judgement of the attending clinician taking into account a variety of factors, i.e., the age and weight of the individual being treated, the mode of administration, and the type and severity of the bacterial infection being prevented or reduced and the potency of the specific compound administered. Typically, the dosage administered per day will be in the range of from about 1 to 250 mg/kg and preferably from about 5 to 20 mg/kg in divided dosages. Typically, the dosage will be administered in dosage units containing convenient amounts, for example, 125, 250 or 500 mg of active ingredient combined with a suitable physiologically acceptable carrier or diluent.

As used herein, "pharmaceutically acceptable salts" means alkali metal salts such as sodium and potassium salts; alkaline earth metal salts such as calcium, magnesium and aluminum salts; amine salts formed from a wide variety of suitable organic amines, i.e., aliphatic, cycloaliphatic, (cyloaliphatic)aliphatic or araliphatic primary, secondary or tertiary mono-, di- or polyamines, or heterocyclic bases, e.g., salts derived from triethylamine, 2-hydroxyethylamine, di-(2-hydroxyethyl)amine, tri-(2-hydroxyethyl)amine, 4-aminobenzoic acid-2-diethylaminoethyl ester, 1-ethylpiperidine, bicyclohexylamine, N,N'-dibenzylethylenediamine, pyridine, collidine, quinoline, procaine, dibenzylamine, 1-ephenamine and N-alkylpiperidine, acid addition salts formed from mineral acids such as hydrochloric, hydrobromic, hydroiodic, phosphoric or sulfuric acids, or formed from organic carboxylic or sulfonic acids such as trifluoroacetic, para-toluene sulfonic, maleic, acetic, citric, oxalic, succinic, benzoic, tartaric, fumaric, mandelic, ascorbic and malic acids. The compounds of this invention contain a 3-carboxylic group and a basic group (the heterocyclic group) which form an inner salt, i.e., a Zwitterion.

"Pharmaceutically acceptable esters" means physiologically cleavable esters, i.e., metabolizable esters known in the penicillin, cephalosporin and penem arts to be easily cleaved within the body to the parent acid. Examples of such esters are indanyl, phthalidyl, methoxymethyl, glycyloxymethyl, phenylglycyloxymethyl, thienylglycyloxymethyl, acetoxymethyl and pivaloyloxymethyl.

Preparation of the foregoing salts and esters may be carried out according to conventional procedures for forming salts of beta-lactams such as penicillins, cephalosporins and penems. Salts of the compound can be formed, for example, by treating with metal compounds such as alkali metal salts of suitable carboxylic acids, or with ammonia or a suitable organic amine, wherein preferably stoichiometric amounts or only a small-excess of the salt-forming agent is used. Acid addition salts of the compound are obtained in the usual manner, for example, by treating with an acid or a suitable anion exchange reagent. Inner salts of the compounds of formula A, i.e., a zwitterion, may be formed by neutralizing salts such as acid addition salts to the isoelectric point. The esters are preparable in a manner analogous to the preparation of the corresponding esters of penicillins and cephalosporins.

Salts may be converted in the usual manner into the free carboxy compounds.

The compounds of this invention are prepared by the processes disclosed in U.S. patent application Ser. No. 445,295, filed Nov. 29, 1982, and in U.S. patent application Ser. No. 549,535, filed Nov. 7, 1983. The process disclosed in Ser. No. 549,535 referred to as process C is preferred for preparing the compounds of this invention. The process comprises:

(a) reacting an azetidinone of the formula

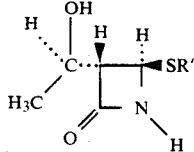

wherein R' is a sulfur protecting group selected from triphenylmethyl, 2-pyranyl, or lower alkyl carbonyl; with an α-substituted allyl acetate of formula II

WCH$_2$CO$_2$CH$_2$CH=CH$_2$     II wherein W is a leaving group; to form the intermediate of formula III

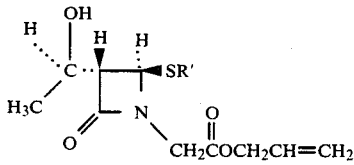

wherein R' is as defined above;

(b) treating the compound of formula III with a stoichiometric excess of elemental zinc in a strong acid to deprotect the sulfur and form the compound of formula IV

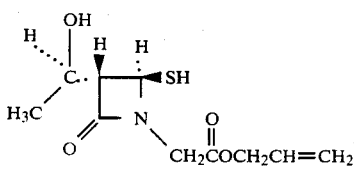

(c) treating the compound of formula IV with a hydroxy protecting group to form the compound of formula V

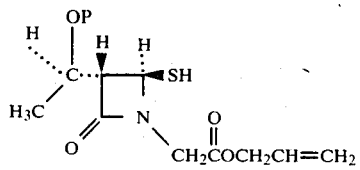

wherein P is a removable hydroxy protecting group as hereinabove defined;

(d) reacting the compound of formula IV or V with a thiocarbonyl compound of formula VI

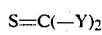     VI wherein Y is a leaving group to form a compound of formula VII

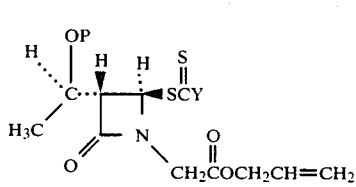

wherein Y and P are as hereinabove defined;

(e) treating compound VII with a non-nucleophilic strong base to form a compound of formula VIII(a) which is tautomeric with formula VIII(b)

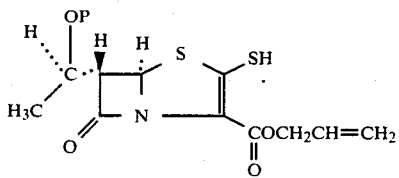

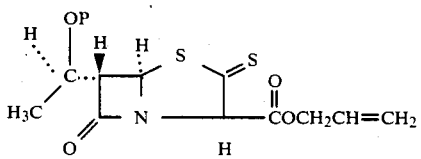

wherein P is as hereinabove defined;

(f) treating the compounds of formulas VIII(a) and VIII(b) under conditions which effect removal of the hydroxy protecting group to form the compounds of formula IX(a) and IX(b).

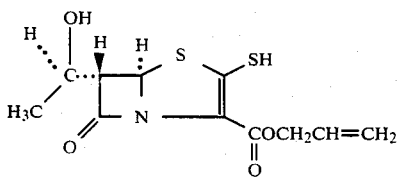

-continued

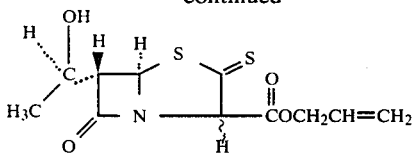
IX(b)

(g) reaction of the compound of formulas IX(a) and IX(b) with either a compound of the formula X

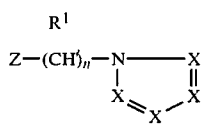
X wherein X, R$^1$ and n are as defined hereinabove and Z is a leaving group, e.g. CH$_3$SO$_2$—O, halogen, O$^-$—P$^+$(C$_6$H$_5$)$_3$, or with a compound of the formula XI

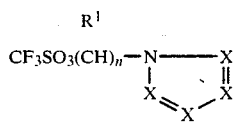
XI wherein X, R$^1$ and n are hereinabove defined to form a compound of formula XII

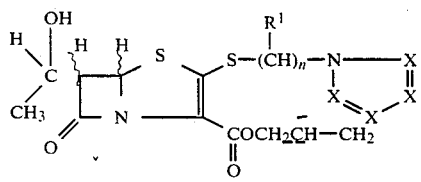
XII wherein X, R$^1$ and n are defined above.

(h) treatment of a compound of formula XIII under catalytic conditions to remove the allyl protecting group in the presence of an alkali base (if the product is a zwitterion, deprotection requires only the catalyst and any mild nucleophile, e.g., H$_2$O, alcohol, etc.) to form the compounds of formula A

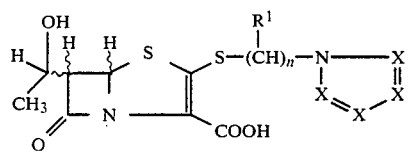
A wherein X, R$^1$ and n are as hereinabove defined.

In a preferred embodiment the α-substituted allyl acetate of formula II is added to the azetidinone of formula I to form the intermediate of formula III. The intermediate of formula III is then utilized directly in steps (b) and (c) which are conducted sequentially without isolation of any intermediates.

Likewise steps (d) and (e) are preferably conducted sequentially without the necessity of isolating any intermediates.

Step (a) involves the reaction of an azetidinone of formula I at 15°-30° C. in the presence of an acid acceptor with an α-substituted allyl acetate of formula II to form the compound of formula III. Preferred W leaving groups in the compound of formula II include tosyl, mesyl, chloro, bromo, iodo, and trifluoromethanesulfonyl. Particularly preferred W leaving groups are iodo and bromo.

Where the solvent utilized is also an acid acceptor, for instance, pyridine, no additional reagent is utilized. Alternatively, an organic solvent such as acetonitrile may be employed. In these cases, a separate acid acceptor, organic or inorganic must be added to the system. Preferably, the reaction is conducted in acetonitrile employing cesium carbonate or tetra alkyl ammonium hydroxide as the acid acceptor.

Step (b) involves the conversion of the compound of formula III to the corresponding thiol of formula IV by deprotecting the sulfur with a stoichiometric excess of elemental zinc in hydrochloric acid in a suitable organic solvent (e.g. tetrahydrofuran, dimethylformamide) at −15° to 25° C., preferably at about 0° C.

Step (c) involves the protection of the 6-hydroxy substituent. Hydroxy protecting groups are well known in the beta lactam art. A particularly preferred reagent for this step is bis trimethyl silylacetamide which readily forms the trimethylsilyl protecting group at the 6-hydroxy moiety. Preferably step (c) is conducted directly upon the completion of step (b) without isolation of the intermediate of formula IV. Thus the inert solvent utilized, e.g. DMF, may be the same as the one used in step (b). Solvents such as chloroform, methylene chloride and the like may also be employed in step (c). Temperatures for the reaction of step (c) range from 0° C. to 30° C.

Step (d) involves the reaction of the compound of formula V with the thiocarbonyl reagent of formula VI which has the structure S=C(—Y)$_2$ wherein Y is a leaving group. Typical of such leaving groups are chloro, bromo, iodo, imidazolyl and acyloxy such as naphthyloxy. For the purposes of this process, 1,1'-thiocarbonyldiimidazole or beta-naphthyloxythiocarbonylchloride are preferred thiocarbonyl reagents. Typically, this step (d) is conducted directly upon the completion of step (c) without isolation of the intermediate of formula V. Thus, the solvent utilized may be the same as the one used in step (c). Temperatures for the reaction of step (d) range from about 10° C.–45° C., with room temperature (about 25° C.) being generally preferred.

Step (e) involves the cyclization of the compound of formula VII into the thione of formulas VIII(a) and VIII(b). The reaction is typically conducted in an anhydrous inert organic solvent such as tetrahydrofuran and the like. An essentially equimolar amount of a strong base such as lithium diisopropyl amide (LDA), lithium di-(trimethylsilyl) amine and the like is added to the system to effect cyclization. Typically, the reaction is conducted at from −50° to −100° C. and preferably at −70° C. and is generally complete from within 5 minutes to 24 hours.

Step (f) involves the removal of the 6-hydroxy protecting group in the compound of formulas VIII(a) and VIII(b) to form the compound of formulas IX(a) and IX(b).

Methods for the removal of this group are well known in the β-lactam art. Preferably, when the 6-hydroxy protecting group is trimethylsilyl, addition of a mild aqueous acid solution, such as acetic acid, to the same solution as is employed in step (e) effects removal.

The term "removable hydroxy protecting group" as used herein means any such group conventionally used for this purpose, with the only requirement being compatibility with the hydroxy substituent on the penems and removability utilizing elemental zinc or any other conventional agent for this purpose which will not adversely affect the penem structure. For the purpose of this invention, preferred hydroxy protecting groups include trichloroethoxycarbonyl, dimethy-t-butylsilyl, trimethylsilylethoxycarbonyl and trimethylsilyl.

Step (g), wherein the compound of formulas IX(a) and IX(b) is reacted with compounds of formula X or XI, is conducted in an inert atmosphere, such as nitrogen, in an organic solvent such as tetrahydrofuran (THF). The reaction is completed within 1 to 3 hours to yield allyl-2-(heterocycloalkylthio)-6-(1-hydroxyethyl)-penem-3-carboxylate.

Compounds of formula X wherein $R^1$ is lower alkyl substituted by groups such as cyano or halogen may be prepared from compounds of the formula XIII

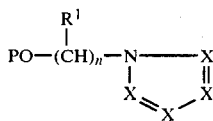

XIII wherein $R^1$ is hydroxyloweralkyl and P, X and n are as defined above. The hydroxy of $R^1$ is mesylated, and the mesyl group is displaced by the appropriate cyano- or halogen-containing reagent, e.g. sodium cyanide or hydrogen fluoride. The protected oxygen is then deprotected and functionalized to the appropriate Z group.

Removal of the allyl group in Step (h) is effected by the addition of the above allyl ester to a solution containing palladium (zero) and an alkali alkylcarboxylate, carboxylic acid or aqueous carbonate. This is described by McCombie in U.S. Pat. No. 4,314,942 which is incorporated herein by reference. Under these conditions, the removal of the allyl group and formation of the alkali salt or the free acid of the compound occurs The following examples illustrate the preparation of the compound and compositions of this invention.

EXAMPLE 1

PREPARATION OF ALLYL (5R,6S,8R)-2-THIOL-6-(1-HYDROXYETHYL)-PENEM-3-CARBOXYLATE AND ALLYL (5R,6S,8R)-2-THIOCARBONYL-6-(1-HYDROXYETHYL)PENEM-3-CARBOXYLATE (A) Preparation of (3S,4R)-1-(allyloxycarbonylmethyl)-3-(1-hydroxyethyl)-4-(triphenylmethylthio)azetidin-2-one Add 3 gm of (3S,4R)-3-(1-hydroxyethyl)-4-(triphenylmethylthio)azetidin-2-one to 10 ml of acetonitrile containing 0.286 gm of cesium carbonate. Add 0.2 gm of α-iodo allyl acetate to the system. Stir the system at room temperature for 16 hours. Dilute with ether (50 ml), filter and wash the ether layer with 1% aqueous phosphoric acid, followed by water. After drying over sodium sulfate remove solvent to give a foamy solid.

(B) Preparation of (3S,4R)-3-(1-hydroxyethyl)-1-allyloxycarbonylmethyl-4-sulfhydryl-azetidin-2-one Add 500 mg of (3S,4R)-1-(allyloxycarbonylmethyl)-3-(1-hydroxyethyl)-4-(triphenylmethylthio)azetidin-2-one and 20 ml tetrahydrofuran to a 50 ml flask. Add zinc dust and 10% hydrochloric acid in small portions over 1 hour until all of the starting material is reacted. Recover the product by filtering off the excess zinc and removing the solvent to crystallize the title product.

NMR: (CDCl$_3$)=6.2–5.7(1H, m); 5.5–5.15 (2H, m); 5.0 (1H, dd, J=3,9 c/s); 4.75–4.55 (2H, m); 4.45–3.95 (1H, m); 4.14(1H, d, J=18 c/s); 3.78(1H, d, J-18 c/s); 3.19(1H, dd, J=6,3 c/s); 2.09(1H, d, J=9 c/s); 1.34 (3H, d, J-6 c/s).

(C) Preparation of (3S,4R)-3-(1-trimethylsilyloxyethyl)-1-allyloxycarbonylmethyl-4-sulfhydryl-azetidin-2-one Add the entire amount of (3S,4R)-3-(1-hydroxyethyl)-1-allyloxycarbonylmethyl-4-sulfhydryl-azetidin-2-one produced in step (B) above to 25 ml of methylene chloride. To this system add 1.1 ml of bis silylacetamide. Stir the system at room temperature for 15 minutes to give the title compound.

(D) Preparation of (3S,4R)-1-(allyloxycarbonylmethyl)-3-(1-trimethylsilyloxyethyl)-4-(1-imidazolylthiocarbonylthio)azetidin-2-one After completion of step (C) above and to the same solution add 350 mg of thiocarbonyldiimidazole. Stir the system at room temperature for 3 hours. Filter the solution and wash the precipitate with methylene chloride. Collect the filtrate and remove the methylene chloride by stripping. Chromatograph the residue on silica gel eluting with 20% ethyl acetate/methylene chloride to yield 335 mg of the title compound.

NMR: δ=8.4, 1H, s; 7.65, 1H, d(J=1 Hz); 7.05, 1H (dJ=1 Hz); 5.95, 1H, d (J=2 Hz); 5.8, 1H, m; 5.45–5.1, 2H, m; 4.3, 1H, m; 4.1, 2H, Q(J=16 Hz); 3.5, d d (J=2,6); 1.35; 3H, d (J=6 Hz).

(E) Preparation of (5R,6S,8R) allyl-2-thiol-6-(1-trimethylsilyloxyethyl)penem-3-carboxylate and (5R,6S,8R) allyl-2-thiocarbonyl-6-(1-trimethylsilyloxyethyl)penam Add 170 mg of (3S,4R)-1-(allyloxycarbonylmethyl)-3-(1-trimethylsilyloxyethyl)-4-(1-imidazolylthiocarbonylthio)azetidin-2-one to 40 ml of anhydrous tetrahydrofuran under a nitrogen atmosphere. Cool the system to −78° C. and then add 0.6 ml of 1 M lithium di(trimethylsilyl) amine in hexane dropwise to the system. Stir the system at −78° C. for 5 minutes. Add 0.2 ml of acetic acid to the system. Dilute the system to 200 ml with methylene chloride. Wash the organic solution with water, aqueous sodium bicarbonate solution and again with water. Purify the product by chromatography by rapidly eluting the sample through silica gel with 5% ethyl acetate/methylene chloride to afford 125 mg of the desired products and the desilylated products.

(F) Preparation of (5R,6S,8R) Allyl-2-thiol-6 -(1-hydroxyethyl)penem-3-carboxylate and (5R,6S,8R) Allyl-2-thiocarbonyl-6-(1-hydroxyethyl)penam To a 25 ml flask add the entire mixture produced in step (E) along with 5 ml of tetrahydrofuran, 1 ml of water and 1 ml of acetic acid. Stir the system at room temperature for 2 hours. Add ethyl acetate to the solution and wash the organic phase with sodium bicarbonate solution, water and then brine. Dry the organic phase over anhydrous sodium sulfate, filter and remove the solvent by stripping to give the title compound.

EXAMPLE 2

5R,6S,8R-2-[2-(IMIDAZOL-1-YL)ETHYLTHIO]-6-[1-HYDROXYETHYL)PENEM-3-CARBOXYLIC ACID

(1) (A) Preparation of Hydroxyethylimidazole

Dissolve 10 g imidazole and 20 g ethylene carbonate in 20 ml toluene, heat at reflux for 5 hours, cool, and remove top layer. With cooling, add 15 ml concentrated hydrochloric acid to the bottom layer, then extract the excess ethylene carbonate with chloroform. Add potassium carbonate to make basic, extract with 5×50 ml chloroform, dry over sodium sulfate and evaporate the solvent in vacuo. Distill under reduced pressure to obtain hydroxyethylimidazole, b.p. 134°–136° C./0.5 mm.

(B) Preparation of Bromoethylimidazole

Dissolve 1.1 g of hydroxyethylimidazole in 10 ml chloroform. Cool in an ice bath, add a solution of 2.28 g thionyl bromide in 5 ml chloroform and stir for 30 minutes. Stir another hour at room temperature, then pour the resultant mixture into 15 ml cold water and neutralize with sodium bicarbonate. Separate the chloroform layer and retain; extract the aqueous layer with 15 ml chloroform. Combine chloroform solutions, dry over sodium sulfate and evaporate the solvent to obtain bromoethylimidazole.

(C) Preparation of Allyl(5R,6S,8R)-2-[2-(imidazol-1-yl)ethylthio]-6-(1-hydroxyethyl)penem-3-carboxylate To a solution of 0.5 g of the thione prepared in Example 1 in 10 ml tetrahydroduran (THF), add 0.7 g bromoethylimidazole, followed by 2.0 ml of a 5% sodium bicarbonate solution, and stir at room temperature for 3 hours or until thin layer chromatography (ethyl acetate/THF, 50/50) indicates no starting material is left. Evaporate the THF in vacuo, add 10 ml water to the resultant residue and extract with 2×20 ml methylene chloride. Dry the organic layer over sodium sulfate and concentrate in vacuo to an oil. Purify the crude oil by column chromatography (silica gel, eluted with 5% methanol in methylene chloride) to obtain 100 ml of the title compound of Step C.

(D) Preparation of (5R,6S,8R)-2-[2-(Imidazol-1-yl)ethylthio]-6-(1-hydroxyethyl)penem-3-carboxylic acid Under argon, add 100 mg of the allyl ester of Step C to 10 ml methylene chloride, followed by 25 mg triphenyl phosphine, 45 ml 2-ethyl hexanoic acid, and 10 mg Pd° reagent. Let stand until the reaction is complete as shown by thin layer chromatography (5% methanol in methylene chloride as solvent). Extract the resultant product with 2×10 ml water, then wash the aqueous layer with 3×10 ml methylene chloride. Lyophilize the aqueous layer to obtain 73 mg of crude title compound.

Purifying the product by reverse phase column chromatography (25 g silica gel eluted with water) to obtain 53 mg of the title compound:

NMR - (D$_2$O)=8.65 (1H,s), 7.4 (2H,d), 5.3 (1H,s), 4.4 (2H,m), 4.05 (1H,m), 3.7 (1H,d), 3.3 (2H, m), 1.5 (3H,d).

(2) Alternatively, prepare the title compounds as follows:

(A) Preparation of Hydroxyethylimidazole
See Step 1A, above.

(B) Preparation of Bromoethylimidazole Hydrobromide Salt

Dissolve 5.2 g of the product of Step A in 25 ml methylene chloride. Cool in an ice bath, add 3.85 ml thionyl bromide in 10 ml methylene chloride and stir for 1 hour. Evaporate the solvent in vacuo and use the resultant residue without further purification.

(C) Preparation of Allyl (5R,6S,8R)-2-[2-(imidazol-1-yl)ethylthio]-6-(1-Hydroxyethyl)Penem-3-Carboxylate Dissolve 3.0 g of the thione prepared in Example 1 in 30 ml THF and 10 ml water. Add a solution of 5.12 g bromoethylimidazole hydrobromide salt in 20 ml THF and 20 ml water, followed immediately by 3 g sodium bicarbonate in 10 ml water. Stir at room temperature for 2½ hours or until thin layer chromatography (30% ethyl acetate in methylene chloride) indicates the reaction is complete. Add 100 ml water to the resultant mixture and extract with 2×100 ml ethyl acetate. Dry the organic layer over sodium sulfate and concentrate in vacuo.

Purify as in Step 1C, second paragraph, to obtain the title compound.

(D) Preparation of 5R,6S,8R-2-[2-(Imidazol-1-yl)ethylthio]-6-(1-hydroxyethyl)penem-3-carboxylate Acid
See Step 1D, above.

EXAMPLE 3

SODIUM (5R,6S,8R)-2-[2-(1,2,4-1H-TRIAZOL-1-YL)ETHYLTHIO]-6-(1-HYDROXYETHYL)PENEM-3-CARBOXYLATE (A) Preparation of Hydroxyethyltriazole Dissolve 3.2 g potassium tert-butoxide in 40 ml methanol, add 2.0 g 1,2,4-triazole and 3.6 g 2-bromoethanol and stir overnight. Evaporate the solvent in vacuo. Dissolve the residue in ethyl acetate and purify by column chromatography (silica gel, elute with methylene chloride changing to 10% methanol in methylene chloride). Combine fractions containing more polar product as shown by TLC and evaporate the solvent in vacuo to obtain the title compound of Step A.

(B) Preparation of Bromoethyltriazole Hydrobromide Salt

Stir 600 mg of the product of Step A and 1.1 g thionyl bromide in 6 ml of chloroform under a nitrogen atmosphere for 1½ hours. Evaporate the solvent in vacuo. Dry the resultant residue under high vacuum for 15 minutes to obtain the title compound.

(C) Preparation of Allyl (5R,6S,8R)-2-[2-(1,2,4-1H-triazol-1-yl)ethylthio]-6-(1-hydroxyethyl)penem-3-carboxylate In a manner similar to that described in Example 2, Step C, first paragraph, substitute bromoethyltriazole hydrobromide salt for the bromoethylimidazole HBr salt to obtain the title compound. Slurry in hot ethyl acetate, cool and filter to obtain the title compound:

NMR-90 mHz (CD$_3$CN) - =8.22 (1H,s), 7.92 (1H,s), 6.3–5.6 (1H,m), 5.69 (1H,d,J-1.5 Hz), 5.65–5.08 (2H,m), 4.8–4.6 (2H,m), 4.5–4.4 (2H, m), 4.3–3.9 (1H,m), 3.78 (1H,dd,J=1.5 Hz, 6 Hz), 3.6–3.2 (2H,m), 1.23 (3H,d,J=6 Hz)

(D) Preparation of Sodium (5R,6S,8R)-2-[2-(1,2,4-1H-triazol-1-yl)ethylthio]-6-(1-hydroxyethyl)penem-3-carboxylate Under nitrogen, stir 160 mg of the product of Step C, 0.1 ml pyridine and 0.265 ml 2-ethylhexanoic acid in 6 ml acetonitrile for 1 hour. Evaporate the solvent in vacuo at 40° C. or lower. Add methylene chloride and water to the resultant residue. Separate the water layer and extract the methylene chloride layer with 3×20 ml water. Combine the aqueous layer and wash with methylene chloride. Evaporate the water in vacuo to obtain the title compound:

NMR-90 mHz (D$_2$O) - =8.5 (1H,s), 8.13 (1H,s), 5.51 (1H,d,J=1.5 Hz), 4.7–4.5 (2H,m), 4.4–4.05 (1H,m), 3.83 (1H,dd,J=1.5, 6 Hz), 3.7–3.15 (2H,m), 1.29 (3H,d,J=6 Hz).

EXAMPLE 4

(5R,6S,8R,2(R,S))-2-[1-METHYL-2-(IMIDAZOL-1-YL)ETHYLTHIO]-6-(1-HYDROXYETHYL)-PENEM-3-CARBOXYLIC ACID (A) Preparation of (2-Hydroxy)propylimidazole Mix 6.8 g imidazole and 15.3 g propylene carbonate and heat at 140° C. for 1 hour. Chromatograph the resultant residue on silica gel, eluting with methylene chloride:ethyl acetate (1:1), then with 5→10% methanol in methylene chloride to obtain the title compound of step A.

(B) Preparation of Allyl(5R,6S,8R,2(R,S))-2-[1-methyl-2-(imidazol-1-yl)ethylthio]-6-(1-hydroxyethyl)-penem-3-carboxylate Dissolve 0.5 g of the product of Step A in 2 ml methylene chloride and add the resultant solution to a mixture of 0.8 ml trifluoromethanesulfonic anhydride and 0.83 ml diisopropylethyl amine in 10 ml methylene chloride at 0° C. Let stir 30 minutes, then add the resultant mixture to a solution of 1 g of the thione prepared in Example 1 in 10 ml tetrahydrofuran, 10 ml water, and 0.3 g sodium bicarbonate. Stir at room temperature until thin layer chromatography (methanol:methylene chloride, 1:9) indicates no starting material is left. Evaporate the solvent in vacuo and partition the resultant residue between water and methylene chloride. Dry the organic layer over magnesium sulfate and evaporate the solvent in vacuo. Purify the resultant residue in silica gel, eluting with 25% ethyl acetate/methylene chloride 100% ethyl acetate to obtain the title compound of Step B.

NMR-(CDCl$_3$)- $\delta$=7.44(1H,s); 6.95(1H,s); 6.87(1H,s); 6.15–5.65(1H,m); 5.59 (d,J=2c/s); 5.5(d,J=2c/s); 5.5–5(2H,m); 4.75–4.52(2H,m); 4.3–3.95(3H,m); 1.5–1.1(6H,m).

(C) Preparation of (5R,6S,8R,2(R S))-2-[1-methyl-2-(imidazol-1-yl)ethylthio]-6-(1-hydroxyethyl)penem-3-carboxylic acid Treat the product of Step B in a manner similar to that described in Example 2, Step D to obtain the title compound.

M.S. (FAB) - M+1=356

EXAMPLE 4A

Separation of (5R,6S,8R,2R) and (5R,6S,8R,2S)-2-[1-METHYL-2-(IMIDAZOL-1-YL)ETHYLTHIO]-6-(1-HYDROXYETHYL)-PENEM-3-CARBOXYLIC ACID Chromatograph the product of Example 4 on a Whatman M90DS3 reverse phase high pressure liquid chromatography column, eluting with acetonitrile:water (12:88). Combine the appropriate fractions as determined by TLC and evaporate the solvent to obtain the pure diastereomers.

EXAMPLE 5

(5R,6S,8R,2(R,S))-2-[1-CYANOMETHYL-2-(IMIDAZO-1-YL)ETHYLTHIO]-6-(1-HYDROXYETHYL)PENEM-3-CARBOXYLIC ACID (A) Preparation of Epiimidazolo hydrin Cool to 0° C. a solution of 9 g sodium imidazole in 40 ml dimethylformamide, add 13.7 g epibromohydrin in 40 ml dimethylformamide, and warm to room temperature for 30 minutes. Evaporate the solvent in vacuo and purify the resultant residue on silica gel, eluting with tetrahydrofuran, to obtain the title compound of Step A.

(B) Preparation of 3-Hydroxy-4-(imidazol-1-yl)butyronitrile

Dissolve 12.4 g of the product of Step A in 25 ml dimethylsulfoxide, add 4.9 g sodium cyanide in 25 ml dimethylsulfoxide, and warm to 50° C. Evaporate the solvent in vacuo and purify the resultant residue on silica gel using tetrahydrofuran→20% methanol in tetrahydrofuran to obtain the title compound of Step B.

(C) Preparation of allyl(5R,6S,8R,2(R,S))-2-[1-Cyanomethyl-2-(imidazol-1-yl)ethylthio)-6-(1-hydroxyethyl)penem-3-carboxylate Treat the product solution of Step B in a manner similar to that described in Example 4, Step B, substituting triethylamine for diisopropylethylamine and cooling to −78° C. in the first part, and reacting with the thione at 0° C. to obtain the title compound of Step C.

Alternatively, dissolve the residue of Step B in 50 ml methylene chloride at 0° C., add 1.2 equivalents of triethylamine, 1 equivalent of methanesulfonyl chloride, and warm to room temperature for 30 minutes. Evaporate the solvent in vacuo, extract the resultant residue with tetrahydrofuran and continue with the reaction with the thione as described in Example 4, Step B.

(D) Treat the product of Step C in a manner similar to that described in Example 2, Step D to obtain the title compound.

EXAMPLE 6

(5R,6S,8R,2(R,S))-2-[1-HYDROXYMETHYL-2-(IMIDOZOL-1-YL)ETHYLTHIO]-6-(1-HYDROXYETHYL)PENEM-3-CARBOXYLIC ACID (A) Preparation of (1-(2,3-Ethoxypropyloxy)-1-ethoxy)-ethane Dissolve 40 g glycidol in 1 liter methylene chloride, add 40 g ethyl vinyl ether and cool to 2° C. Add 250 mg p-toluenesulfonic acid and warm slowly to room temperature. Evaporate the solvent in vacuo and distill the residue at 2mm Hg (b.p. 39°–41° C.) to obtain the title compound of Step A.

(B) Preparation of (1-Ethoxy-1-(2-hydroxy-3-(imidazol-1-yl)propoxy)ethane

Dissolve 16.6 g imidazole in 75 ml dimethylformamide, add 35.82 g of the product of Step A and heat slowly to 120° C. Cool the resultant mixture to room temperature. Evaporate the solvent in vacuo, partition the resultant residue between methylene chloride and water (125 ml/125 ml), extract once with water, then evaporate the organic layer in vacuo to obtain the title compound of Step B.

(C) Preparation of (1-Ethoxy-1-(2-methylsulfonyloxy-3-(imidazol-1-yl)-propoxy)ethane To 40 g of the product of Step B in 30 ml methylene chloride, add 3.2 ml triethylamine and 1.6 ml methanesulfonyl chloride. Stir at room temperature for 1 hour, then extract the resultant mixture with water (2×50 ml) and evaporate the organic layer in vacuo to obtain the title compound of Step C.

(D) Preparation of (1-Ethoxy-1-(2-mercapto-3-(imidazol-1-yl)propoxy)ethane

To 4.25 g of the product of Step C in 25 ml dimethylformamide, add 5.25 g sodium thioacetate, and stir 48 hours at room temperature. Evaporate the solvent in vacuo, dissolve the resultant residue in 100 ml methylene chloride, filter and evaporate the methylene chloride in vacuo. Dissolve the residue in 100 ml ethanol, saturate with ammonia and let stand at room temperature for 1 hour. Evaporate the solvent in vacuo, partition the resultant residue between water and methylene chloride, then remove the methylene chloride in vacuo. Purify the resultant residue on silica gel, eluting with ethyl acetate:methylene chloride (1:1) to obtain the title compound of Step D.

(E) Preparation of Allyl (5R,6S,8R)-2-ethylsulfinyl-6-(1-hydroxyethyl)penem-3-carboxylate Dissolve 2 g of allyl (5R,6S,8R)-2-ethylthio-6-(1-hydroxyethyl)penem-3-carboxylate in 80 ml methylene chloride at −5° C., add 2 g calcium carbonate, then 1.1 g m-perbenzoic acid in 20 ml methylene chloride. After 20 minutes, extract the reaction mixture with 100 ml water, separate and evaporate the organic layer to obtain the title compound of Step E.

(F) Preparation of Allyl(5R,6S,8R,2(R,S))-2-[1-(ethoxy-1-ethoxy)-methyl-2-(imidazol-1-yl)ethylthio]-6-(1-hydroxyethyl)-penem-3-carboxylate Dissolve 500 mg of the product of Step E in a mixture of 4 ml acetonilrile and 2 ml water, add 100 mg sodium bicarbonate, then 700 mg of the product of Step C and let stand 1 hour. Partition the resultant mixture between methylene chloride and water, evaporate the methylene chloride and purify the resultant residue on a silica gel column using methylene chloride:tetrahydrofuran (1:1) to obtain the title compound of Step F.

Alternatively, react the mesylate of Step C directly with the thione of Example 1 in a manner similar to that described in Example 4, Step B.

(G) Dissolve 174 mg of the product of Step F in 10 ml of a mixture of water:tetrahydrofuran (1:1), then adjust to pH 3 with a 5% aqueous solution of p-toluenesulfonic acid. Let stand 1.5 hours, evaporate the solvent in vacuo and partition the resultant residue between 5% aqueous sodium bicarbonate and methylene chloride. Evaporate the organic layer, redissolve the resultant residue in 10 ml methylene chloride, and continue with the procedure described in Example 2, Step D, to obtain the title compound.

EXAMPLE 7

(5R,6S,8R,2(R,S))-2-[1-FLUOROMETHYL-2-(IMIDAZOL-1-YL)ETHYLTHIO]-6-(1-HYDROXYETHYL)PENEM-3-CARBOXYLIC ACID (A) Preparation of Allyl(5R,6S,8R,2(S,R))-2-[1-fluoromethyl-2-(imidazol-1-yl)ethylthio]-6-(1-hydroxyethyl)penem-3-carboxylate Dissolve 0.100 g of the product of Step 6G and 0.05 g of calcium carbonate in 5 ml of methylene chloride at −78° C. Add 0.043 gm of diethylaminosulfur trifluoride and stir for 30 minutes. Dilute with ethyl acetate, then stir with water for 5 minutes at 0° C. Separate the organic layer, wash with water, and evaporate the solvent. Chromatograph the resultant residue on silica gel, eluting with methylene chloride:ethyl acetate to obtain the title compound of Step A.

(B) Preparation of (5R,6S,8R,2(S,R))-2-[1-Fluoromethyl-2-(imidazol-1-yl)ethylthio]-6-(1-hydroxyethyl)penem-3-carboxylic acid Treat the product of Step A in a manner similar to that described in Example 2, Step D, to obtain the title compound.

EXAMPLE 8

(5R,6S,8R,2(R,S))-2-[2-HYDROXY-3-(IMIDAZOL-1-YL)PROPYLTHIO]-6-(1-HYDROXYETHYL)-PENEM-3-CARBOXYLIC ACID (A) Preparation of Allyl(5R,6S,8R,2(R,S))-2-[2-hydroxy-3-(imidazol-1-yl)propylthio]-6-(1-hydroxyethyl)penem-3-carboxylate Slowly combine epiimidazolohydrin as prepared in Example 5, Step A with 600 mg of the thione prepared in Example 1 in 2 ml dimethylformamide and stir until thin layer chromatography (on silica gel eluted with methanol:methylene chloride (1:9)) shows no more thione present. Partition the resultant solution between water and methylene chloride, evaporate the organic layer and purify the resultant residue on a silica gel column, eluting with 5→10% ethanol in methylene chloride.

(B) Treat the product of Step A in a manner similar to that described in Example 2, Step D, to obtain the title compound.

M.S. (FAB) - M+1=372

EXAMPLE 9

(5R,6S,8R)-2%l -[2-(4-HYDROXYMETHYLIMIDAZOL-1-YL)ETHYLTHIO]-6-(1-HYDROXYETHYL)PENEM-3-CARBOXYLIC ACID (A) Combine 8g of 4-hydroxymethylimidazole hydrochloride and 9.8 g t-butyldimethylsilyl chloride in 60 ml. dry dimethylformamide (DMF). Add 17.4 ml triethylamine over 5 minutes and stir the mixture for 1 hour. Add methylene chloride, wash with water and evaporate the organic layer to dryness.

(B) Dissolve 6.3 g of the residue of Part A and 3.3 g potassium t-butoxide in 25 ml DMF, cool to 0° C., add 3.89 ml of ethyliodoacetate, and stir the reaction mixture for 1 hour. Add methylene chloride, wash with water, and evaporate the remaining DMF in vacuo. Chromatograph the resultant residue on a coarse silica gel column, eluting with ethyl acetate:methylene chloride. Combine the appropriate eluent fractions to give two solutions, one comprising a more polar component and the other a less polar component as determined by TLC. Evaporate the solvent from each component in vacuo.

(C) Dissolve 1.5 g of the less polar component from Part B in 15 ml freshly distilled THF and cool at 0° C. Add 95 mg lithium aluminum hydride, stir for 1 hour, add aqueous ammonium chloride, and extract 5 times with ethylacetate. Evaporate the solvent in vacuo and purify the resultant residue by chromatography on a coarse silica gel column, eluting with ethyl acetate; evaporate the solvent in vacuo.

(D) Dissolve 500 mg of the product of Part C in 15 ml methylene chloride and add 0.352 ml triethylamine and 0.164 ml mesyl chloride. Stir 30 minutes, add 25 ml methylene chloride, wash twice with water, once with brine, dry the solution over anhydrous sodium sulfate and evaporate the solvent in vacuo. Chase with toluene to remove residual triethylamine. Add the resultant residue to 40 ml methylethyl ketone and 1 g sodium iodide, heat to reflux for 7 minutes, then cool to room temperature and proceed to part E.

(E) Combine the product of Part D with 1 g sodium thione in 20 ml THF 20 ml water, and 100 mg sodium bicarbonate. Stir for 1 hour, evaporate most of the solvent in vacuo, add methylene chloride, and wash with sodium bicarbonate, water, and then brine. Purify the resultant crude residue by chromatography on coarse silica gel, eluting with methylene chloride methanol:-methylene chloride (3:97).

(F) Combine 950 mg of the product of Part E, 12.5 ml THF, 12.5 ml water and 100 mg p-toluene sulfonic acid. Stir 2 hours, evaporate most of the solvent, add 4 equivalents of sodium bicarbonate and stir another 10 minutes. Extract 5 times with methylene chloride, add sodium chloride and extract 5 more times with methylene chloride. Combine extracts and evaporate in vacuo to obtain a residue.

NMR-(CDCl$_3$) $\delta$=7.5 (1H,s); 6.8(1H,s); 6.2–5.7 (1H,m); 5.63 (1H,d, 2c/s); 5.54–5.1 (2H,m); 4.92 (2H,s); 4.8–4.4 (3H,m); 4.4–4(2H,m); 3.69(1H,dd,J=7,2c/s); 3.5–3(2H,m); 1.3 (3H,d, J=6c/s).

(G) Treat the product of Part F in a manner similar to that described in Example 2, Part D to obtain (5R,6S,8R)-2-[2-(4-hydroxymethylimidazol-4-yl)ethyl-thio]-6-(1-hydroxyethyl)penem-3-carboxylic acid.

NMR-(D$_2$O) $\delta$=8.8(1H,s); 7.56(1H,s); 5.57 (1H,d,J=2c/s); 5.14 (2H,s); 3.95 (1H,dd,J=6,2c/s); 3.67–3.2(2H,m); 1.3 (3H,d,J=6c/s).

EXAMPLE 9A (5R,6S,8R)-2-[2-(5-HYDROXYME-THYLIMIDAZOL-1-YL)ETHYLTHIO]-6-(1-HYDROXYETHYL)PENEM-3-CARBOXYLIC ACID (A) Treat the more polar component from Example 9A, Part B in a manner similar to that described in Example 9A, Parts C-F to obtain a residue.

NMR-(CDCl$_3$) $\delta$=7.4 (1H,s); 6.8 (1H,s); 6.15–5.63 (1H,m); 5.55 (1H, d,J=2c/s); 5.5–5.05 (2H,m); 3.66 (1H,dd,J=7,2cs); 3.5–3.15 (2H, m); 1.3 (3H,d,J=6c/s).

(B) Treat the product of Part A in a manner similar to that described in Example 2, Part D to obtain the title compound.

EXAMPLE 10

(5R,6S,8R)-2-[2-(4-AMINOMETHYLIMIDAZOL-1YL)ETHYLTHIO]-6-(1-HYDROXYETHYL)-PENEM-3-CARBOXYLIC ACID FORMATE (A) Dissolve 2.4 g of tritylamine in 80 ml freshly distilled DMF; add over 3–5 minutes 4 g 4-chlorome-thylimidazole hydrochloride in 15 ml water. Stir 1¼ hours, add 9 g of potassium carbonate in 20 ml water and stir 20 minutes. Reduce the solvent volume in vacuo, add methylene chloride, and wash twice with water, then pour the organic layer into hexane to precipitate a crude product. Add the resultant residue to methylene chloride, heat and then cool the resultant solution to precipitate 4-tritylaminomethylimidazole.

(B) Dissolve the product of Part A in dry ethanol, add dropwise to 1 equivalent of sodium ethoxide and stir 1 hour. Evaporate the solvent in vacuo, add DMF and 1 equivalent of ethyliodoacetate and stir overnight. Add methylene chloride, wash 5 times with water and evaporate the organic layer to obtain a residue. Chromatograph the resultant residue on coarse silica gel, eluting with ethylacetate. Combine the appropriate fractions to give two solutions, one comprising a more polar component and the other a less polar component as determined by TLC. Evaporate the solvent from each component in vacuo.

(C) Dissolve 1.4 g of the less polar component from Step B in 25 ml freshly distilled THF and add slowly an excess of lithium aluminum hydride (as determined by TLC). After 15 minutes, add acetone to react with the excess lithium reagent, then remove the solvent. Add methylene chloride to the resultant residue and wash with water. Evaporate the organic solvent and chromatograph the resultant residue on coarse silica gel, eluting with ethylacetate→methanol:ethylacetate (10:90); combine the appropriate fractions and evaporate the solvent.

(D) Treat the residue obtained in Part C in a manner similar to that described in Example 9, Part D.

(E) Treat the product of Part D in a manner similar to that described in Part E of Example 9, eluting the column with ethyl acetate→methanol:ethyl acetate (5:95).

NMR: (CDCl$_3$) $\delta$=6.1–5.55 (1H,m); 5.5 (1H,d, J=2c/s); 5.45–5.05 (2H,m); 4.6 (2H,m); 4.2–3.8 (3H,m); 3.58 (1H,dd,J=7,2c/s); 3.45–2.5 (5H,m); 1.2 (3H,d,J=6c/s).

M.S. (FAB)- M+1=653

(F) Treat the product of Part E in a manner similar to that described in Part D of Example 2, adding an excess of 98% formic acid (as determined by TLC) to the methylene chloride solution before extracting with water to obtain 5R,6S,8R-2-[2-(4-aminomethylimidazol-1-yl)ethylthio]-6-(1-hydroxyethyl)penem-3-carboxylic acid formate.

M.S. (FAB)- M+1=371

EXAMPLE 10A (5R,6S,8R)-2-[2-(5-AMINOMETHYLIMIDAZOL-1-YL)ETHYLTHIO]-6-(1-HYDROXYETHYL)-PENEM-3-CARBOXYLIC ACID FORMATE (A) Treat the more polar component of Example 10, Part B in a manner similar to that described in Example 10, Parts C-E to obtain a residue.

NMR: (CDCl$_3$) $\delta$=6.1–5.6 (1H,m); 5.53 (1H,d, J=2c/s); 5.46–5.03 (2H,m); 4.6 (2H,m); 4.4–3.85 (3H,m); 3.62 (1H,dd,J=7, 2c/s); 3.5–2.8 (5H,m); 1.28 (3H,d,J=6c/s).

(B) Treat the product of Part A in a manner similar to that described in Example 10, Part F to obtain the title compound.

EXAMPLE 11

(5R,6S,8R)-2-[4- and 5-ACETIMIDOME-THYLIMIDAZOL-1-YL)ETHYLTHIO]-6-(1-HYDROXYETHYL)PENEM-3-CARBOXYLIC ACID (A) Dissolve 20 mg of the product of Example 10, Part F in 2 ml water, add 30 drops of acetic anhydride and stir for 30 minutes. Evaporate the solvent in vacuo, dissolve the resultant residue in water and lyophilize to obtain the 4-acetimidomethylimidazolyl isomer of the title compound.

M.S. (FAB)- M+1=413

(B) Treat 20 mg of the product of Example 10A, Part B in a manner similar to that described in Part A to obtain the 5-acetimidomethylimidazolyl isomer of the title compound.

EXAMPLE 12

(5R,6S,8R,2(R,S))-2-[1-AMINOMETHYL-2-(IMIDAZOL-1-YL)ETHYLTHIO]-6-(1-HYDROX-YETHYL)PENEM-3-CARBOXYLIC ACID (A) Dissolve 0.5 mole of sodium imidazole in 300 ml of DMF, cool to 0° C., and slowly add 0.5 mole epibromohydrin in 200 ml of DMF. Stir 30 minutes, then add THF/hexane (1500 ml/500 ml) and filter. Evaporate the solvent at 90° C., extract quickly with THF and filter to obtain epiimidazolo hydrin in THF.

(B) To 200 ml of the solution obtain in Part A, add 45 ml aminodiphenylmethane and remove the solvent. Heat the resultant residue to 60° C. for 3 hours. Add 150 ml methylene dichloride, filter, add 1 liter of hexane and remove the methylene dichloride in vacuo; let the resultant solution stand until clear and decant the hexane. Repeat the procedure until the product is free of aminodiphenylmethane. Purify the resultant residue by column chromatography on silica gel, eluting with methylene chloride→methanol:methylene chloride (5:95). Combine the appropriate fractions and evaporate the solvent to obtain (1-diphenylmethylamino-2-hydroxy-3-(imidazol-1-yl))propane.

(C) Dissolve 200 mg of the product of Part B in 3 ml THF, add 260 mg 1,1'-thiocarbonyldiimidazole and stir overnight at room temperature. To the resultant solution, add 5 ml water, stir 15 minutes, and partition the resultant solution with water/methylene chloride. Separate the organic layer, evaporate the solvent in vacuo, and purify the resultant residue on a silica gel column, eluting with methylene chloride→methanol:methylene chloride (2:98). Combine the appropriate fractions and evaporate the solvent in vacuo.

(D) Under nitrogen, heat 2.8 g of the product of Part C at 200° C. for 1½ hours. Purify the resultant product on a silica gel column, eluting with methylene chloride→methanol:methylene chloride (10:90). Combine the appropriate fractions and evaporate the solvent in vacuo.

(E) Add 98% formic acid to 1.5 g of the product of Part D and stir for 4 days, then reflux the mixture for 3 hours. Remove the formic acid under nitrogen. Add methylene chloride, sodium bicarbonate and 2 drops of water and stir for 1 hour. Purify the resultant residue on silica gel as described in Part D.

(F) Combine 200 mg of the product of Part E with 2 ml of allyl alcohol and 250 mg sodium and stir overnight. Add carbon dioxide (solid) and remove the solvent. Extract the resultant residue with methylene chloride and filter.

(G) Combine 250 mg of the product of Example 6, Part E, 1 ml water, 1 ml acetonitrile and 100 mg sodium bicarbonate; add the product of Part F and let stand 30 minutes. Treat the resultant reaction mixture as described in Example 6, Part F.

NMR-(CDCl$_3$) δ- 7.57 (1H,s); 6.96 (2H,s); 3.9-3.3 (3H,m); 1.3 (3H,d, J=6c/s).

(H) Treat the product of Part G in a manner similar to that described in Example 2, Part D to obtain the title compound.

M.S. (FAB)- M+1=371

EXAMPLE 13

(5R,6S,8R)-2-[2-(4- or 5-METHYLIMIDAZOL-1-YL)ETHYLTHIO]-6-(1-HYDROXYETHYL)PENEM-3-CARBOXYLIC ACID (A) Combine 8.2 g of 4-methylimidazole and 3 equivalents of ethylene carbonate; heat slowly to 120° C. for 2 hours. Chromatograph the resultant residue on silica gel, eluting with methylene chloride→methanol:methylene chloride (10:90). Combine the appropriate fractions and evaporate the solvent.

(B) Dissolve 3 g of the product of Part A in 30 ml methylene chloride, add 4.0 ml triethylamine and cool to 0° C. Slowly add 2.0 ml mesyl chloride, warm to room temperature and let stand 30 minutes. Partition the resultant mixture with brine/ethyl acetate. Separate the organic layer and evaporate the solvent to obtain a residue.

(C) Dissolve 3.9 g of the product of Part B in 100 ml methyl ethyl ketone, add 3 equivalents of sodium iodide and reflux for 10 minutes. Cool the resultant solution, partition with brine/ethyl acetate, separate the organic layer, evaporate the solvent at low temperatures and immediately dilute with THF. Use the resultant solution immediately in Part D.

(D) Add the product of Part C in portions to a solution of 2.0 g of the product of Example 1, Part F and 1 g sodium bicarbonate in 25 ml THF and 25 ml water until no thione is left (monitor by TLC). Partition the resulting solution with methylene chloride/water, separate the organic layer and evaporate the solvent. Recrystallize the resultant residue from methylene chloride.

NMR-(CDCl$_3$) δ- 7.44 (1H,s); 6.68 (1H,s); 6.25-5.5 (1H,m); 5.58 (1H, d,J=2c/s); 5.6-5.15 (2H,m); 4.85-4.65 (2H,m); 4.4-4 (3H,m); 3.75 (1H,dd,J=6,2c/s); 3.45-3.05 (2H,m); 2.25 (3H,s); 1.38 (3H,d,J=6c/s).

(E) Treat the product of Part D in a manner similar to that described in Example 2, Part D to obtain the title compound.

M.S. (FAB)- M+1=356

NMR-(D$_2$O) δ=8.4 (1H,s); 7.05 (1H,s); 5.3 (1H,d,J=2c/s); 4.45-3.8 (3H,m); 3.58 (1H,dd,J=6, 2c/s); 3.4-2.9 (2H,m); 2.16 (3H,s); 1.1 (3H,d,J=6c/s).

By following the procedures outlined in the above examples, the following compounds of this invention may be prepared:

Compounds of the formula

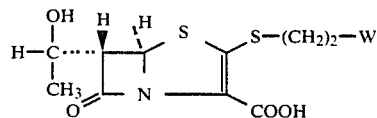

wherein W is

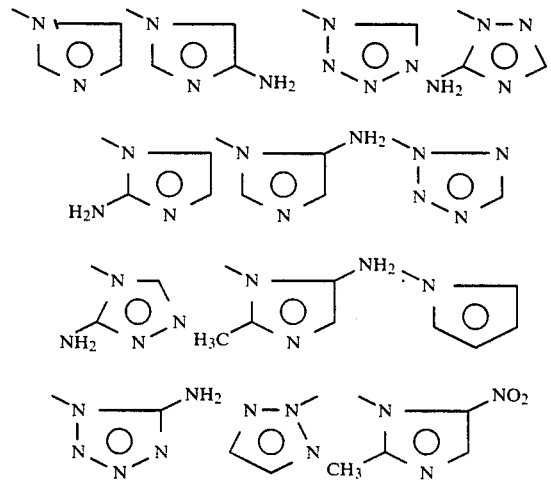

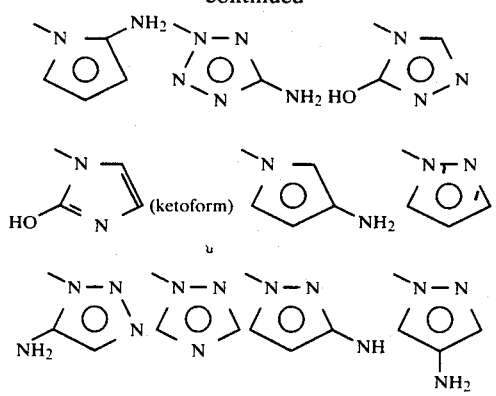
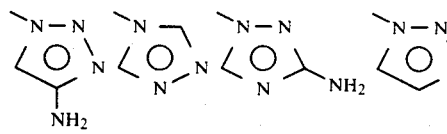
Compounds of the formula
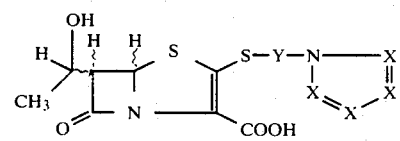
wherein x is as defined above and Y is
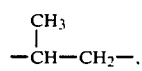 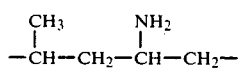 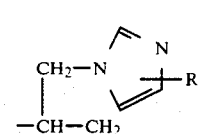 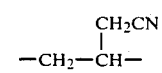
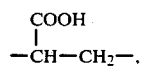 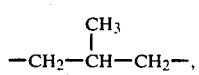 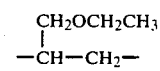 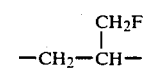
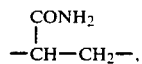 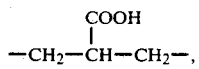  
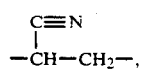 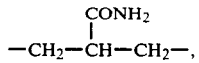 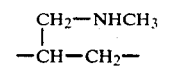 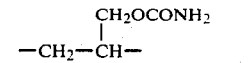
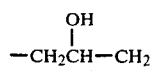 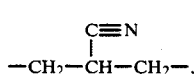 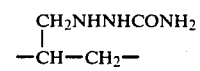 
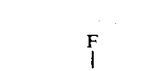 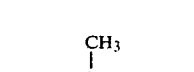  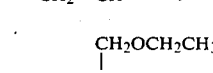
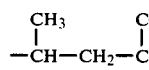 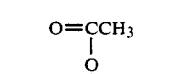 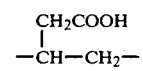 
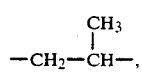 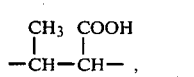 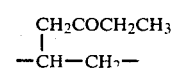 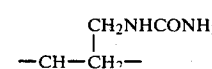
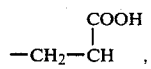 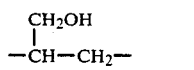 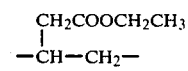 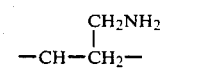
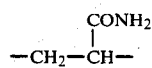 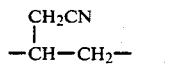 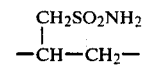 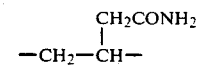
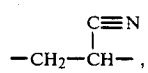 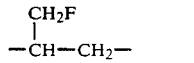 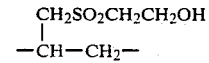 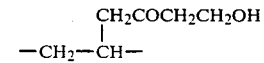

$$-CH_2-\underset{\underset{NH_2}{|}}{CH}-CH_2-,$$

$$-CH_2-\underset{\underset{\underset{CH_3}{|}}{\overset{\overset{CH_3}{|}}{O}}}{CH}-CH_2-,$$

$$-\underset{\underset{CH_2OCONH_2}{|}}{CH}-CH_2-$$

$$-CH_2-\underset{\underset{CH_2OH}{|}}{CH}-$$

$$-CH_2-\underset{\underset{CH_2SO_2CH_2CH_3}{|}}{CH}-$$

$$-\underset{\underset{CH_2-NH_2}{|}}{CH}-CH_2-$$

$$-CH_2-\underset{\underset{CH_2SO_3H}{|}}{CH}-$$

$$-CH_2-\underset{\underset{CH_2SO_3CH_2CH_3}{|}}{CH}-$$

In the following examples, the Active Ingredient is 5R,6S,8R-2-[2-(imidazol-1-yl)ethylthio]-6-(1-hydroxyethyl)penem-3-carboxylic acid or an equivalent amount of any of its pharmaceutically acceptable salts and esters.

EXAMPLE 14

Injectable Solution

| Ingredient | mg/ml | mg/ml |
|---|---|---|
| Active Ingredient | 100 | 500 |
| Methylparaben | 1.8 | 1.8 |
| Propylparaben | 0.2 | 0.2 |
| Sodium Bisulfite | 3.2 | 3.2 |
| Disodium Edetate | 0.1 | 0.1 |
| Sodium Sulfate | 2.6 | 2.6 |
| Water for Injection q.s. ad | 1.0 ml | 1.0 ml |

Method of Manufacture

1. Dissolve parabens in a portion (85% of the final volume) of the water for injection at 65°–70° C.
2. Cool to 25.35° C. Charge and dissolve the sodium bisulfite, disodium edetate and sodium sulfate.
3. Charge and dissolve the active ingredient.
4. Bring the solution to final volume by adding water for injection.
5. Filter the solution through 0.22μ membrane and fill into appropriate containers.
6. Terminally sterilize the units by autoclaving.

EXAMPLE 15

Injectable Powder: (per vial)

|  | g/vial | g/vial |
|---|---|---|
| Active Ingredient | 0.5 | 1.0 |

Add sterile water for injection or bacteriostatic water for injection for reconstitution.

We claim:

1. Compounds of the formula

[Chemical structure showing penem with OH, CH3, S, COOH, and S-(CH)n-N-X ring with R1 substituent]

wherein each x is $$=\underset{\underset{R}{|}}{C}-$$

or =N—, with the proviso that at least one X is $$=\underset{\underset{R}{|}}{C}-;$$

R is hydrogen, lower alkyl, amino lower alkyl, mono- and di-lower alkyl amino lower alkyl, carboxy lower alkyl, sulfoalkyl, hydroxyalkyl, cyano, hydroxy, amino, mono- and di-lower alkyl amino, alkyl sulfonate, sulfamyl, halogeno, hydroxyliminoloweralkyl, lower alkoxyiminoloweralkyl, carboxy, carbamoyl, mono- or di-lower alkyl carbamoyl, nitro, carbamoyloxy, ureido lower alkyl, or carbamoylhydrazolower alkyl;

$R^1$ is hydrogen, lower alkyl, carboxy, carbamoyl, cyano, hydroxy, amino, lower alkylthio, fluoro, lower alkoxy, or lower alkanoyloxy, provided that when $R^1$ is attached to a carbon atom adjacent to S or N, $R^1$ is not hydroxy, amino, or fluoro; or $R^1$ is lower alkyl substituted by hydroxy, cyano, halogen, lower alkoxy, carbamoyloxy, —$SR^2$, imidazolyl, substituted imidazolyl wherein the substituents are as defined by R, amino, amino substituted by lower alkyl, lower alkyl carbonyl, carbamoyl, mono-alkyl substituted carbamoyl or ureido, carboxy, carbamoyl, mono-alkyl substituted carbamoyl, lower alkylcarbonyl, lower alkoxycarbonyl, hydroxy lower alkyl carbonyl, sulfo, sulfamyl, lower alkyl thio, lower alkylsulfonyl, lower alkoxysulfonyl, or hydroxy lower alkylsulfonyl;

$R^2$ is a substituted or unsubstituted heterocyclyl radical selected from the group consisting of benzothiazolyl, oxazinyl, pyridyl, purinyl, imidazolyl, pyrrolyl, thiazolyl, thiadiazolyl, benzimidazolyl, triazinyl, thiazinyl, furyl, thienyl, triazolyl, tetrazolyl and pyrimidyl, wherein there can be one or more substitutents which can be the same or different and (a) are on a ring carbon or heteroatom, and are independently selected from the group consisting of lower alkyl, —$NR^3R^4$, and lower alkylene-$NR^3R^4$, wherein $R^3$ and $R^4$ are independently selected from the group consisting of hydrogen and lower alkyl, or (b) are on a ring carbon atom only and are selected from the group consisting of =O, hydroxy, lower alkoxy, —$COOR^5$ or halogen, wherein $R^5$ is hydrogen;

n is 1 to 4; and the pharmaceutically acceptable salts and pharmaceutically acceptable esters thereof, in racemic or opticaly active form.

2. Compounds of claim 1 wherein

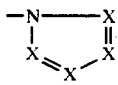

is selected from the group consisting of unsubstituted or substituted pyrrolyl, imidazolyl, pyrazolyl, 1,2,4-triazolyl, 4,1,2-triazolyl, 1,2,3-triazolyl, 2,1,3-triazolyl, 1,2,3,4-tetrazolyl, and 2,1,3,4-tetrazolyl, wherein the substituents are 1 to 4 R groups, and wherein R is as defined in claim 1.

3. Compounds of claim 2 wherein the substituents R are amino, hydroxy, lower alkyl, or hydroxy lower alkyl.

4. Compounds of claim 2 wherein

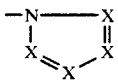

is represented by the formula

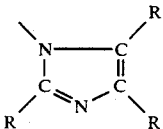

wherein R is as defined in claim 2.

5. A compound of claim 4 wherein each R is hydrogen.

6. A compound of claim 1 wherein n is 2.

7. A compound of claim 1 wherein $R^1$ is hydrogen.

8. A compound of claim 1 wherein $R^1$ is substituted lower alkyl.

9. A compound of claim 4 wherein n is 2 and $R^1$ is hydrogen.

10. A compound of claim 4 wherein n is 2 and $R_1$ is substituted lower alkyl.

11. A compound of claim 8 which is 5R,6S,8R-2-[2-(imidazol-1-yl)ethylthio]-6-(1-hydroxyethyl)penem-3-carboxylic acid.

12. A compound of claim 3 which is sodium 5R,6S,8R-2-[2-(1,2,4-1H-triazol-1-yl)ethylthio]-6-(1-hydroxyethyl)-penem-3-carboxylate.

13. A compound of claim 1 which is 5R,6S,8R-2-[2-(1,2,3-triazol-1-yl)ethylthio]-6-(1-hydroxyethyl)penem-3-carboxylic acid.

14. A compound of claim 1 which is 5R,6S,8R-2-[2-(2-methyl-5-nitroimidazol-1-yl)ethylthio]-6-(1-hydroxyethyl)penem-3-carboxylic acid.

15. A compound of claim 1 which is 5R,6S,8R-2-[2-(tetrazol-1-yl)ethylthio]-6-(1-hydroxyethyl)penem-3-carboxylic acid.

16. A compound of claim 1 which is 5R,6S,8R-2-[2-(tetrazol-2-yl)ethylthio-6-(1-hydroxyethyl)penem-3-carboxylic acid.

17. A compound of claim 1 which is 5R,6S,8R-2-[1-(R,S)-methyl-2-(imidazol-1-yl)ethylthio]-6-(1-hydroxyethyl)penem-3-carboxylic acid.

18. A compound of claim 17 which is 5R,6S,8R,2R-2-[1-methyl-2-(imidazol-1-yl)ethylthio]-6-(1-hydroxyethyl)penem-3-carboxylic acid.

19. A compound of claim 17 which is 5R,6S,8R,2S-2-[1-methyl-2-(imidazol-1-yl)ethylthio]-6-(1-hydroxyethyl)penem-3-carboxylic acid.

20. A compound of claim 1 which is 5R,6S,8R-2-[2-(4-methylimidazol-1-yl)ethylthio]-6-(1-hydroxyethyl)-penem-3-carboxylic acid.

21. A compound of claim 1 which is 5R,6S,8R-2-[2-(5-methylimidazol-1-yl)ethylthio]-6-(1-hydroxyethyl)-penem-3-carboxylic acid.

22. A compound of claim 1 which is 5R,6S,8R-2-[2-(4-hydroxymethylimidazol-1-yl)ethylthio]-6-(1-hydroxyethyl)penem-3-carboxylic acid.

23. A compound of claim 1 which is 5R,6S,8R-2-[2-(5-hydroxymethylimidazol-1-yl)ethylthio]-6-(1-hydroxyethyl)penem-3-carboxylic acid.

24. A compound of claim 1 which is 5R,6S,8R,2(R,S)-2-[1-fluoromethyl-2-(imidazol-1-yl)ethylthio]-6-(1-hydroxyethyl)penem-3-carboxylic acid.

25. A compound of claim 1 which is 5R,6S,8R,2(R,S)-2-[1-hydroxymethyl-2-(imidazol-1-yl)ethylthio]-6-(1-hydroxyethyl)penem-3-carboxylic acid.

26. A compound of claim 1 which is 5R,6S,8R,2(R,S)-2-[1-cyanomethyl-2-(imidazol-1-yl)ethylthio]-6-(1-hydroxyethyl)penem-3-carboxylic acid.

27. A compound of claim 1 which is 5R,6S,8R,2(R,S)-2-[2-hydroxy-3-(imidazol-1-yl)propylthio]-6-(1-hydroxyethyl)penem-3-carboxylic acid.

28. A compound of claim 1 which is 5R,6S,8R,2(R,S)-2-[1-methyl-2-(5-methylimidazol-1-yl)ethylthio]-6-(1-hydroxyethyl)penem-3-carboxylic acid.

29. A compound of claim 1 which is 5R,6S,8R,2(R,S)-2-[1-methyl-2-(4-methylimidazol-1-yl)ethylthio]-6-(1-hydroxyethyl)penem-3-carboxylic acid.

30. A pharmaceutical composition comprising an anti-bacterial effective amount of a compound of claim 1 in admixture with a pharmaceutically acceptable carrier therefor.

31. A method of preventing bacterial infections in warm blooded animals in need of such treatment which comprises administering an antibacterial effective amount of a compound of claim 1.

32. A composition according to claim 30 wherein said antibacterial compound is 5R,6S,8R-2-[2-(4-hydroxymethylimidazol-1-yl)ethylthio]-6-(1-hydroxyethyl)-penem-3-carboxylic acid.

33. A composition according to claim 30 wherein said antibacterial compound is 5R,6S,8R-2-[2-(5-hydroxymethylimidazol-1-yl)ethylthio]-6-(1-hydroxyethyl)-penem-3-carboxylic acid.

34. A parenteral composition according to claim 30.

* * * * *